United States Patent
Hiesinger et al.

(10) Patent No.: US 10,094,749 B2
(45) Date of Patent: Oct. 9, 2018

(54) STORAGE, COLLECTION OR ISOLATION DEVICE

(75) Inventors: Margit Hiesinger, Wuppertal (DE); Vera Holländer, Unna (DE); Markus Müller, Dormagen (DE); Karin Schulte, Düsseldorf (DE); Andre Schrader, Düsseldorf (DE)

(73) Assignee: QIAGEN GmbH, Hilden (DE)

( * ) Notice: Subject to any disclaimer, the term of this patent is extended or adjusted under 35 U.S.C. 154(b) by 705 days.

(21) Appl. No.: 13/810,157

(22) PCT Filed: Jul. 13, 2011

(86) PCT No.: PCT/EP2011/061955
§ 371 (c)(1),
(2), (4) Date: Jan. 16, 2013

(87) PCT Pub. No.: WO2012/007503
PCT Pub. Date: Jan. 19, 2012

(65) Prior Publication Data
US 2013/0105393 A1 May 2, 2013

(30) Foreign Application Priority Data
Jul. 14, 2010 (EP) .................................... 10007273

(51) Int. Cl.
*G01N 1/40* (2006.01)

(52) U.S. Cl.
CPC ............. *G01N 1/40* (2013.01); *G01N 1/4005* (2013.01); *Y10T 29/49* (2015.01)

(58) Field of Classification Search
CPC .................................................. G01N 1/4005
See application file for complete search history.

(56) References Cited

U.S. PATENT DOCUMENTS

| 4,244,694 A | 1/1981 | Farina et al. |
| 4,486,315 A | 12/1984 | Teipel |

(Continued)

FOREIGN PATENT DOCUMENTS

| DE | 2 125 027 A1 | 12/1971 |
| EP | 0 268 946 A2 | 6/1988 |

(Continued)

OTHER PUBLICATIONS

Planned Obsolescence, *The Economist*, pp. 1-3 (Mar. 23, 2009) downloaded from http://www.economist.com/node/13354332/print on Dec. 14, 2015.

(Continued)

*Primary Examiner* — Krishnan S Menon
*Assistant Examiner* — Bradley R Spies
(74) *Attorney, Agent, or Firm* — Seed IP Law Group LLP (57) ABSTRACT

The present invention refers to a device, comprising a hollow body having at least one open end and at least one barrier inside or at the end of the hollow body, which is non-permeable for liquids and solids under ambience conditions, however, becomes liquid-permeable by applying an external force like pressure, drag force or driving power to said barrier, the use of such a device for collection, storage, treatment or isolation of a biomolecule or biomolecules containing samples, a method for preparation of said device and a method for isolation or purification of any biomolecules using said device.

18 Claims, 2 Drawing Sheets

(56) References Cited

U.S. PATENT DOCUMENTS

| | | | |
|---|---|---|---|
| 4,515,889 A | 5/1985 | Klose et al. | |
| 4,787,971 A | 11/1988 | Donald | |
| 5,114,858 A | 5/1992 | Williams et al. | |
| 5,354,483 A | 10/1994 | Furse | |
| 5,364,533 A * | 11/1994 | Ogura | A61B 5/1416 210/504 |
| 5,552,325 A | 9/1996 | Nochumson et al. | |
| 6,251,660 B1 * | 6/2001 | Muir | B01L 3/502 422/236 |
| 6,582,665 B2 * | 6/2003 | Faulkner | A61B 10/0096 210/233 |
| 2002/0096469 A1 * | 7/2002 | Faulkner | A61B 10/0096 210/464 |
| 2002/0110495 A1 | 8/2002 | Hunt et al. | |
| 2005/0191760 A1 | 9/2005 | Heath et al. | |
| 2006/0180548 A1 | 8/2006 | Ji | |
| 2007/0292858 A1 | 12/2007 | Chen et al. | |
| 2008/0190830 A1 | 8/2008 | Maltezos et al. | |
| 2008/0300397 A1 | 12/2008 | Kenrick et al. | |
| 2010/0120129 A1 | 5/2010 | Amshey et al. | |
| 2011/0146418 A1 * | 6/2011 | Brevnov | G01N 1/4005 73/863.23 |

FOREIGN PATENT DOCUMENTS

| | | |
|---|---|---|
| EP | 1 990 641 A1 | 11/2008 |
| WO | 01/94574 A2 | 12/2001 |
| WO | 2005/068610 A1 | 7/2005 |
| WO | 2008/150779 A1 | 12/2008 |
| WO | 2009/157435 A1 | 12/2009 |

OTHER PUBLICATIONS

Siddappa et al., "Regeneration of commercial nucleic acid extraction columns without the risk of carryover contamination," *BioTechniques* 42:186-192 (Feb. 2007).

* cited by examiner

STORAGE, COLLECTION OR ISOLATION DEVICE

The present invention refers to a device, comprising a hollow body having at least one open end and at least one barrier inside or at one end of the hollow body, which is non-permeable for liquids and solids under ambience conditions, however, becomes liquid-permeable by applying an external force like pressure, drag force or driving power to said barrier, the use of such a device for collection, storage, treatment or isolation of a biomolecule or biomolecules containing samples, a method for preparation of said device and a method for isolation or purification of any biomolecules using said device.

During the treatment of biological samples, e.g. for isolating or purifying biomolecules from said samples, it is very common that the sample is contacted with any or several liquid(s), optionally incubated to allow any reaction and thereafter interesting parts of the sample are separated from the remainder. Usually the used liquids are added or transferred by pipetting, wherein often several method steps have to be carried out before the interesting biomolecule is obtained in desired form. In any of the steps contamination of the sample may occur, furthermore it is laborious and time-consuming.

Several well-known approaches for biomolecule isolation are described in the state of the art, encompassing the binding of biomolecules to any matrix, like e.g. DNA or RNA binding to columns of nucleic acid binding materials, affinity binding, e.g. of proteins or low molecular molecules, or chromatographic devices separating the biomolecules according to their size or volume. Furthermore the binding of any undesired compounds to separate them from the desired biomolecules is known, like e.g. using Chelex 100 for DNA isolation as described Walsh et. Al, BioTechniques Vol. 10, No 4 (1991) or Burkhart et al 2002, J Biochem Biophys Methods 52 (2002) 145-149.

The object of the present invention was to provide a method and a device for temporary retention of a liquid within said device and further timely defined delivery of said liquid in a method for treatment of a biological sample without a further pipetting step. A further object was to provide a device and a method for collecting, storing and/or treating a liquid containing sample or to contact a sample with at least one or several liquid(s) with less pipetting steps and diminished risk for cross-contamination.

This object is met by providing a device comprising (i) at least one hollow body (1), each hollow body (1) having at least one open end; (ii) at least one barrier (5) which is non-permeable for liquids and solids under ambience conditions, however, becomes liquid-permeable by applying any external force like preferably pressure, drag force or driving power to said barrier (5), placed inside or at one end of the hollow body (1); (iii) optionally at least one liquid permeable element (4) like preferably a porous frit, filter, fleece or membrane inside of the hollow body (1); (iv) optionally at least one removable closing device (6) to seal at least one open end.

Said device can be used for collecting, storing or treating any liquid comprising sample, e.g. a liquid sample comprising a biomolecule of interest and/or for isolating a biomolecule of interest from such a sample or to replace pretreatment for a sample, cleanup, or other parts from an isolation or preparation procedure for biomolecules.

The hollow body (1) of the device can be made of any material suitable for sample collection, storage or treatment, like plastic, metal, glass, porcelain or similar, preferably the body is made of plastic. In particular the body preferably is made of a thermoplastic resin like polypropylene, polyethylene, polypropylene-copolymers, polyvinylchloride, polyurethane, polycarbonate, polyamide, polyimide, polystyrene, polyethyleneterephthalate, polylactide, ethylene-polyvinylacetate, vinylchloride vinylacetate copolymers, polyacetales, polyetheralcohols, vinylacetate copolymers or arylic polymers without being restricted to these.

The hollow body/each of the hollow bodies of the device has at least one open end, which means that at least one end allows to insert something into the hollow body, like e.g. to insert the sample of interest and/or any liquid, or to remove something from the hollow body. Preferably the device has an inlet (2) and an outlet (3), wherein typically the inlet opening is on the "upper" end of the device and the outlet opening is on the "bottom" side of the device. Optionally the device further comprise at least one removable closing device (6), which closes removably at least one of the openings, e.g. the outlet (3) or the inlet (2), or several (optionally differently shaped) closing devices for all the openings.

According to the invention inside of the hollow body (1) the device has at least one barrier (5) of a material which is non-permeable for liquids and solids under ambience conditions, however, becomes liquid-permeable by applying a force to the material, preferably pressure, drag force or driving power. Said at least one barrier (5) is/are in contact with all of the inner side walls of the hollow body (1) and flushes with said side walls, or is/are placed in a holder (7) which flushes with the side walls. Any remaining gap between the barrier (5) or the holder (7) may be sealed with a suitable sealing material.

With "ambience conditions" according to the present application is meant that the barrier material is under the same conditions as the ambience of the device, in particular no external forces are applied to the barrier material. External forces may be increased pressure on at least one of the surfaces or on any of the sides of the barrier (5), drag forces like vacuum or suction, driving forces like centrifugal forces, shaking or dashing, the last two mentioned preferably by utilization of inertia of the mass, or mechanical forces like puncturing, cutting, rupturing or similar. Accordingly the material is under "ambience conditions" during common handling of the device like standing on the table, pipetting steps, incubation steps, heating and/or cooling, shaking or similar. "Increased pressure" means that at least twice the ambient pressure is externally applied to the barrier material. "Increased pressure" does not comprise the slightly increased pressure resulting from any liquid or solid matrix applied to the barrier material, e.g. if a column like a spin column is filled with a liquid or a solid matrix.

With "non-permeable for liquids" is meant that a liquid, e.g. an aqueous solution or water, an alcohol or an organic solution, particularly preferred an aqueous solution, is retained on the surface of the barrier and is not able to pass said barrier under ambience conditions and preferably is not even able to enter, to penetrate or to soak into the barrier material. It is particularly preferred that independent from the time period of contact of the liquid with the barrier said solution cannot pass the barrier as long as no external force is applied.

By applying any of the external forces cited above the material of the barrier (5) becomes liquid-permeable. This means that the material diminishes its barrier character and allows at least any liquid, preferably a solution comprising solved materials, to pass the material. The permeability might be reversible or irreversible after return to ambience conditions. Preferably the permeability is irreversible. Exemplified is this by that the barrier material becomes porous by applying pressure, drag force or driving power, or the barrier material has a predetermined orifice which is closed under ambient conditions, but opens by applying pressure, drag force or driving power. Preferably after porosity is obtained or the orifice opened the barrier remains liquid permeable due to the contained openings, even under ambience conditions. Further the barrier (5) may break, preferably at a predetermined breaking point by applying pressure, drag force or driving power.

A further possibility is that the device comprises inside of the hollow body (1) above or below of the barrier (5) any material or component which punctures, cuts or ruptures the barrier material when an external force like e.g. pressure, drag force or driving power is applied to the device. If the barrier material is punctured, it is preferred that puncturing is micropuncturing, which means that only very small punctures are obtained in the barrier material, not resulting in a rupture of the barrier (5), but making the barrier (5) porous.

With "above" is meant that, if the device is positioned in its use mode, e.g. a column is placed upright in a holder or a cup, the material or component which punctures, cuts or ruptures the barrier material is on the upper side of said barrier material. In particular, if the device is used as intended including any liquid, the the material or component which punctures, cuts or ruptures the barrier material is on the same side as the liquid and is pressed by application of the external force, in particular by applying pressure, drag force or driving power, to the upper surface of the barrier material which as well is in contact with the liquid.

If the material or component which punctures, cuts or ruptures the barrier material is "below" the barrier material the bottom surface of the barrier material will be pressed by the external force to the the material or component which punctures, cuts or ruptures the barrier material. In the latter case the material or component which punctures, cuts or ruptures the barrier material is on the opposite side of the liquid-permeable element (4) as the liquid.

The intensity and type of the applied external force suitable for rendering the barrier (5) liquid permeable depends from the material used for the barrier (5) and optionally from the component or material used for puncturing, cutting or rupturing the barrier (5). It is preferred that the barrier (5) is resistant against any external force up to a predetermined intensity, wherein due to the selected material and due to any treatment of the material the intensity when the barrier (5) becomes liquid permeable varies. For a skilled person it is easy to determine by standard experiments which type of external force and which intensity of any of the forces results in a liquid permeability of the selected materials for the barrier(s) (5). There can be different materials or thickness of the barrier material or a different principle, which results in different intensities of the external force necessary to make the barrier liquid permeable. 1×g, referably to 2×g, more preferred to 5×g, even more preferred to 10×g and particularly preferred to 20×g, 40×g or 50×g. It is particularly preferred that the barrier (s) is 7 are resistant to 100×g. In particular the barrier(s) should be resistant against the forces occurring during pipetting, turning, smooth vortexing and other commonly used process steps.

The barrier (5) is preferably provided in form of a film, foil, coating, septum, membrane, hydrophobic sintered material (hydrophobic frit), a material which was made hydrophobic by chemical or other treatment or any other suitable form serving as an effective barrier. Suitable materials for the barrier (5) are for example hydrophobic filter materials; hydrophobic fiber web materials; membranes, films or foils of plastics, in particular thermoplastic or thermosetting polymers like polyethylene, polypropylene, polypropylene-copolymers, polyvinylchloride, polyurethane, polycarbonate, polyamide, polyimide, polystyrene, polyethyleneterephthalate, polylactide, ethylene-polyvinylacetate, vinylchloride vinylacetate copolymers, polyacetales, polyetheralcohols, vinylacetate copolymers, arylic polymers; or silicone; latex; polysaccharides, in particular cellulose ether and derivatives; thin metal layers like aluminium foil or copper foil, or any other suitable, preferably film-forming material which can be provided as a film, foil, coating, septum or membrane. As films or coatings thermoplastic polymers like polyethylene, polypropylene, polypropylene-copolymers, polystyrene, polyvinylchloride, polyurethane, polycarbonate or polyamide are particularly preferred. As a hydrophobic filter material a hydrophobized polyethylene filter is preferred, as a membrane a hydrophobized fiber membrane like e.g. any of the Filtrona® fiber membranes (Filtrona, Reinbek, Germany) and as a membrane such a material like Gore Tex® or similar is preferred. Any water-resistant but vapour permeable membrane as well is preferred.

Examples for the component or material which punctures, cuts or ruptures the barrier material are: any solid porous, holey or perforated plate providing a rough surface like e.g. a porous frit made of any inert material like e.g. silica or a polymer; a metal sieve having fine needles on its surface; a perforated plate having sharp edges at the perforation sites; a piercing device having sharp edges or (a) needle(s), sand or any other particulate inert material. In a preferred embodiment a porous frit, serving as liquid-permeable element (4) as well is serving as a component puncturing the barrier material, if said barrier (5) is pressed to the element (4) when an external force as described above is applied to the device.

According to one of the simplest embodiments of the present invention the device can represent a hollow body (1) having at least one open end, comprising at one end of the hollow body or preferably inside of the hollow body at least one barrier (5) comprising a material which becomes porous, has a predetermined orifice, or breaks, preferably at a predetermined breaking point by applying pressure, drag force or driving power.

In a preferred embodiment of the present invention the hollow body (1) of the device further comprises inside at least one liquid-permeable element (4) like preferably a porous frit, a filter, a fleece or a membrane. Said liquid-permeable element(s) (4) mainly has/have the function to retain any solid material contained in the hollow body compartment from elution, but to allow any liquid and solved ingredients to pass the element (4). Accordingly e.g. the liquid sample part can be separated from any solid sample part or a liquid sample can be purified by a chromatographic, chelating, absorbing, adsorbing or binding matrix or a filtering material contained and retained in the device. Said liquid permeable element(s) (4) preferably is/are in contact with all of the inner side walls of the hollow body (1) and flushes with said side walls, or is/are placed in holder (7) which flushes with the side walls and/or any remaining gap may be sealed with a suitable sealing material.

At least one of the liquid permeable element(s) (4) can be adjacent to at least one of the barrier(s) (5), wherein "adjacent" means that it is either close to the barrier (5), however, doesn't contact it, or that it is in direct contact with the barrier (5). In case the barrier (5) represents a coating it is preferred that the coating is placed on at least one surface of a liquid-permeable element (4), particularly preferred on one surface of a frit, filter or membrane. In any case the liquid permeable element(s) (4) can be placed above or below of the barrier (5), wherein "above" and "below" is meant in the same sense as described above for the component or material which punctures, cuts or ruptures the barrier material. Preferably the barrier (5) is above the liquid-permeable element (4), which means, that said barrier (5) is adjacent to the upper surface of a liquid-permeable element (4), if the device is positioned in the use mode (inlet (2) up, outlet (3) down).

Particularly preferred the device comprises (i) at least one hollow body (1), each hollow body (1) having an inlet (2) and an outlet (3); (ii) at least one barrier (5) inside of the hollow body, placed above to the outlet (3) or, if present, adjacent of at least one of the liquid permeable element(s) (4); (iii) optionally at least one liquid permeable element like preferably a porous frit, filter, fleece or membrane (4), placed above the outlet (3); (iv) optionally at least one removable closing device (6) to seal the inlet (2) and/or outlet (3) of the hollow body; and (v) optionally at least one collection tube to collect a mobile phase (eluate) after having passed the outlet (3).

Figure 1:
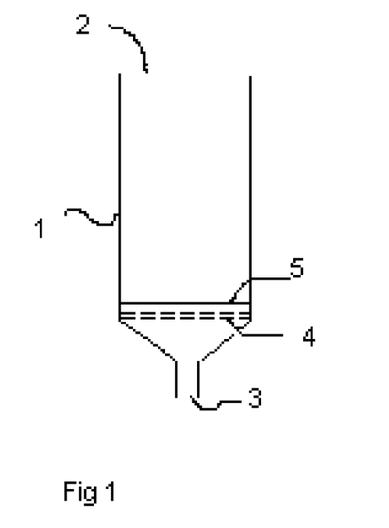
FIG. 1 shows one embodiment of the device of the present invention, which is a spin column comprising a hollow body (1), an inlet (2) and an outlet (3), a porous frit (4) and a polystyrene film (5). The polystyrene film (5) can be as well below the porous frit (4).
Figure 2:
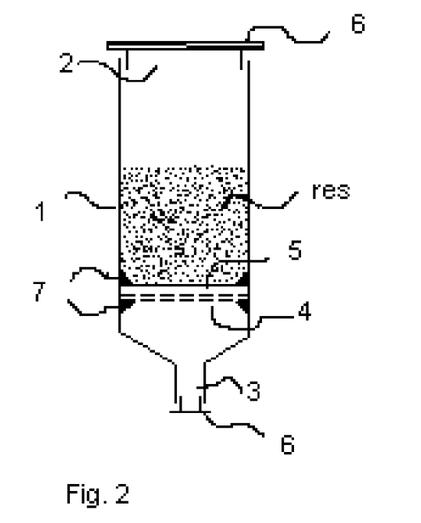
FIG. 2 shows one embodiment of the device of the present invention, which is a spin column comprising a hollow body (1), an inlet (2) and an outlet (3), a porous frit (4), a polyethylene film (5), a holder (7) and two removable closing devices (6), further comprising a particulate resin (res).

Preferably at least one of the barrier(s) (5) and optionally the liquid permeable element(s) (4) is/are placed close to the outlet (3) side of the hollow body, particularly preferred proximate to the outlet (3) of the device. "Proximate to" means that no further reaction compartment of the hollow body is between the barrier (5) or the element (4) and the outlet, however, due to the construction of the device indeed some space might be between the barrier (5) or the element (4) and the end of the device. In FIG. 1 an embodiment is shown where the element (4) adjacent to a barrier (5) is placed "proximate to" of the outlet (3) of the device.

An example according to the present invention is an embodiment wherein at least one non-permeable barrier (5) is placed adjacent to at least one liquid permeable element (4), particularly a porous frit, filter, fleece or membrane which means close to or in direct contact with element (4) inside of a hollow body (1). For further instance at least one non-permeable barrier (5) is placed between at least two of the liquid permeable elements (4) in direct contact with at least one of said elements (4), preferably selected independently from a frit, filter, fleece or membrane.

A further embodiment wherein the preferred properties are achieved is a device comprising several hollow bodies (1) as described above, wherein either each of the hollow bodies (1) are build up similarly or the assembly of the hollow bodies differ from each other, however, at least a part of the hollow bodies fall under the description as defined above.

Although the form of the device is not limiting the present invention, in a preferred embodiment the hollow body/bodies of the device is/are at least partially cylindrical or at least partially conical. Non-limiting examples for embodiments of the invention are reaction tubes, reaction cups, collection tubes, collection containers, a column body, centrifugation tubes, microcentrifuge tubes, in particular compartmented containers like tubes, cups, flasks, chromatographic columns, spin columns, plastic syringe, multi well plates, multiwell blocks, multiwell column plates, flasks, bottles, cups, phiols, collection or centrifugation vessels or similar.

The device can further comprise a removable closing device (6) on at least one of the open ends. Said closing device serves to keep the inside of the device clean and/or sterile or optionally to keep the content of the device inside of the hollow body (1). The closing device (6) can be easily removed before, during and/or after usage of the device. Preferably the closing device (6) is used when the device contains any liquid or flowable or movable solid material. The closing device (6) can be for example a cap, a plug, a cover plate, a film or foil, or any other suitable removable closing device. It can be reclosable or a disposable closing device. The closing devices (6) of an inlet (2) and an outlet (3) side can differ from each other or can be the same type of closing device (6).

The device of the present invention may further comprise any liquid, buffer or solution in the hollow body, wherein said liquid, solution or buffer is prevented from leakage by at least one barrier (5), which means that either the liquid, solution or buffer is between two barriers (5) or the liquid is retained by one barrier (5) and the device comprises at least one closing device (6). Additionally or alternatively the device can comprise a solid material, wherein "solid" means that the material is not dissolved in a liquid, but might be dispersed or suspended in a liquid. The solid material preferably is a particulate material, more preferred a particulate matrix material for chelating, binding, adsorbing, absorbing, filtration, size exclusion or chromatographic separation of a sample, a fiber web or fleece as defined more in detail below.

The device of the present invention can be used for collection, storage or treatment of a sample, particularly of a liquid containing sample. With "liquid sample" is meant that either the sample itself is a liquid, solution, suspension or dispersion, or any gelly, solid or particulate sample or a biological sample as described below is combined with a liquid or solution to obtain a solution, dispersion or suspension. Preferably the device can be used for collection, storage or treatment of a liquid sample comprising any biomolecule, e.g. for isolation of at least one biomolecule from said sample. The liquid can be (temporally) retained in the device and can be released at a desired time by applying an external force to the device as described above.

The liquid or solution can be any aqueous or organic based liquid or solution like water, any aqueous buffer, a cell culture medium, a nutrient solution, an organic solvent or any reaction solution or a mixture thereof. Preferably the solution is an aqueous buffer, wherein the buffer is not restricted to a particular buffer, but is preferably any of the buffers commonly used for cell treatment, or the solution is a cell culture medium or nutrient solution.

A biomolecule according to the present invention is any molecule occurring in a biological sample. A biological sample can be any body fluid or tissue or a human or animal including insects, like blood, plasma, serum, blood fractions like leukocyte fraction or buffy coat, urine, serum, liquor, sputum, sperm, saliva etc, tissue of any organ, brain, skin, muscle etc.; scales; swabs; faeces; keratinic samples like hair, nails, horns or antlers; carapaces or wings (in particular of insects); cell suspensions or cell cultures, cell fragments or cell organelles like chloroplasts or mitochondrions, vesicles, nuclei or chromosomes; samples comprising bacterial, fungal or yeast cells or fragments, any type of virus, viroid or prions; histological samples like punctates or tissue slices; tissue cultures; plants; plant parts, cells or tissue; samples taken from the environment, like e.g. water, dust, air or mud samples; food samples; forensic samples like cigarette filters, textile samples, tooth brush; any solution comprising an prepurified or preisolated biomolecule etc. without being restricted to the mentioned examples.

Accordingly a biomolecule is any nucleic acid like DNA or RNA, in particular lienar, branched or circular, single stranded or double stranded nucleic acids, more particular mRNA, sRNA, miRNA, snRAN, tRNA, hnRNA or ribozymes, genomic, plasmid or organelles DNA; any nucleotide, oligonucleotide or polynucleotide, even synthetic, modified or labeled oligo- or polynucleotides; PCR-primers, short DNA or RNA fragments for hybridization; PNAs (peptide nucleic acids); any protein, peptide or amino acid, including unlabeled or labeled antibodies, receptors, hormones, growth factors and modified proteins, nucleic acids, proteins and peptides of infectious origin; metabolite, any lipid; sugar (monomer, oligomer or polymer); proteoglucanes; any low molecular pathway product, signal molecule, receptor or enzyme activator or inhibitor; agents, medicaments and metabolites of medicaments, medicaments or any other biomolecule of interest.

The present invention comprises further a method for isolation or purification of at least one biomolecule of interest from a sample comprising at least one type of biomolecules, comprising
  (a) placing the sample inside of the hollow body (1) of a device as described above, wherein either the sample is a liquid sample, or the sample is contacted with any liquid before or after placing the sample inside of the hollow body, or the hollow body comprises a liquid coming in contact with the sample when said sample is placed into the device,
  (b) optionally incubating the sample inside of the hollow body (1),
  (c) applying an external force, preferably pressure, drag force or driving power to the sample comprising inner side of the device,
  (d) collecting an eluate comprising the biomolecule of interest.

In step (a) the sample comprising at least one biomolecule of interest is placed into the hollow body (1) of the inventive device. Said sample is either a liquid sample, or the sample is a solid sample like a cell, tissue or any other of the biological samples mentioned above containing less liquid and is contacted with any liquid before or after placing the sample inside of the hollow body, or the hollow body comprises a liquid coming in contact with the sample when said sample is placed into the device. The sample, which is placed to the inventive device, can be a lysate of a biological sample.

In said method according to one preferred embodiment the hollow body (1) of the device may comprise either a solid matrix material or at least one liquid or both before the biomolecule comprising sample is added. For example the device comprises a particulate resin for chromatographic separation of the sample, a binding, absorbing, adsorbing or chelating matrix for specific or unspecific binding, absorption or adsorption of sample compositions, a filtering material, beads for lysis of cells or for binding of cell components, or any other component commonly used for biomolecule isolation or purification. One preferred solid particulate matrix is a chelating resin purifying compounds by ion exchange, chelating e.g. metal ions, in particular transition metal ions. Such a commonly known resin is a styrene-divinylbenzene resin comprising imino diacetic acid groups, sold under the name Chelex 100, (BioRad) which is suitably used for DNA or RNA isolation, wherein the nucleic acids don't bind to said resin. Such a commonly known resin is a styrene-divinylbenzene resin comprising imino diacetic acid groups, sold under the name Chelex 100 (Biorad), which is suitably used for DNA or RNA isolation, wherein the nucleic acids don't bind to said resin. Further any inert material like e.g. agarose, Sephacryl resin, silicone; latex; polysaccharides, cellulose ether and derivatives, thermosetting of thermoplastic polymers, metals or further solid matrices like beads, films, foils, particles etc. may be used. Said materials may comprise functional groups on their surface(s) selectively binding any of the undesired contaminants. A further preferred matrix comprises or consists of a ion exchanging matrix or a matrix comprising specific binding sites for biological compounds. The matrix further may comprise woven or non-woven fibers or a fleece, e.g. of silica, polysaccharides or any other suitable material.

The matrix suitable to separate the contaminants from the desired biomolecules further can comprise or consist of HIC particles (hydrophobic interaction chromatography particles, Dionex Corp., USA), cationic or anionic exchanging material; size exclusion material like agarose; gel filtration material; minerals, like e.g. hydroxylapatit, bentonite, zeolithe, kaolinit, diatomite or processed minerals like silica; InhibitEX® (Qiagen, Hilden, Germany), IDA (iminodiacetic acid), NTA (nitrilo acetic acid), and derivatives of the last two mentioned, a resin or other substrate with IDA or NTA groups or derivates of them, EDTA, specific antibodies, amphipol; charcoal, PVP (polyvinylpyrrolidone); superabsorbing polymers; Non-fat milk cocktails, termed BLOTTO (Bovine Lacto Transfer Technique Optimizer) (in S. H. De Boer* (1995) Nucleic Acids Research, 1995, Vol. 23, No. 13 2567-2568); Polysaccharides, e.g. chitosane, starch, glycogen, cellulose or derivates of them; proteins like specific antibodies or enzymes; without being restricted to the mentioned examples.

It is particularly preferred in the present method that the device comprises a matrix which adsorbes, absorbes, chelates or binds compounds of the biological sample which are undesired for further processing whereas the biomolecule(s) of interest are essentially not adsorbed, absorbed or bound. The compounds which are undesired for the further processing are biomolecules, which shouldn't be isolated in the process on the other hand inhibitors which interfere the downstream processes.

Additionally or alternatively any liquid or solution can be contained, like a lysis buffer for cell lysis, a liquid for tissue dissolution, an organic solvent or any other liquid or solution commonly used during isolation and/or purification of a biomolecule from a sample.

The method comprises an optional incubation step (b) wherein ingredients of the solutions or buffers comprised in the sample are allowed to be active or to react with the biological sample. For example, if the biological sample is a cell containing or tissue containing sample and a lysis buffer was added to said sample, the lysis of the cells or tissue is allowed to occur during an optional incubation step. On the other hand, if a solid matrix material is contained in the hollow body, during the incubation step any binding, chelating, absorption or adsorption of sample ingredients may occur.

In step (c) it is preferred that pressure is applied to the inlet (2) of the device, pressing the biomolecule of interest to the outlet side of the device; or vacuum is applied to the outlet (3) of the device, sucking the biomolecule of interest to the outlet side of the device; or centrifugal forces are applied to the device moving the biomolecule of interest to the outlet side of the device; or a combination of said forces is applied to the device.

As well comprised in the method of the invention is that during the process comprising steps (a) to (c) at any stage additionally any further step is carried out. For example at any stage any additional liquid might be added into the hollow body (1) of the device, e.g. by pipetting the liquid into the hollow body (1) from the inlet (2) side. Furthermore any heating or cooling step may be carried out if appropriate for the intended result. Additionally or alternatively steps for mixing like inverting or shaking might be useful for the intended result.

In step (d) at least one eluate passing the liquid-permeable element (4) is collected. Independent from any further optional steps between step (c) and step (d) the biomolecule of interest can be obtained after applying an external force to the inventive device.

Dependent from the used isolation or purification procedure and the matrix contained in the hollow body (1) of the device the biomolecule of interest may be contained in the first eluate passing the liquid-permeable element (4), or the biomolecule of interest is contained in any later eluate. For example, if the matrix is a binding, absorbing or adsorbing matrix for the biomolecule and any washing steps are comprised in the isolation/purification procedure, the interesting biomolecule is comprised in a later eluate. In this case said eluate either can be obtained by applying again any external force to the device, or the eluate is able to pass the liquid-permeable element by gravitational force only. Preferably the matrix contained in the hollow body is not absorbing, adsorbing or binding the biomolecule of interest, so that the biomolecule is contained in the first eluate obtained by applying an external force to the inventive device.

The device of the present invention can be prepared by placing at least one barrier (5) inside of a hollow body (1) having at least one open end in a way that the barrier (5) or each of the barriers (5) is either in direct contact with all of the inner side walls of the hollow body (1) and flushes with said side walls, or the barrier(s) is/are placed in a holder (7) which is in contact with all of the inner side walls of the hollow body (1) and flushes with said side walls. Any remaining gap between the barrier(s) (5) and the side walls or the holder (7) and the side walls might be filled with an adhesive or sealing material.

In a preferred embodiment additionally to the barrier(s) (5) at least one liquid-permeable element (4) is placed inside of the hollow body (1), preferably adjacent to at least one of the barrier(s) (5). The liquid-permeable element (4) either can be placed inside of the hollow body (1) before the barrier (5) is placed inside, or the barrier (5) is placed inside the hollow body (1) before the liquid-permeable element (4) is placed inside the body (1). In a preferred preparation method of the device at least one liquid-permeable element (4) is brought in contact with at least one barrier (5) material and thereafter the combined "module" of liquid-permeable element (4) and barrier (5) is placed inside of the hollow body. For instance such a "module" can comprise one liquid-permeable element (4), preferably a frit, fleece, filter or membrane and one barrier (5) material, preferably a film, foil or coating, membrane, septum hydrophobic sintered material or hydrophobic fibrous material or it can comprise two liquid-permeable elements (4), wherein between them two at least one barrier (5) material is contained like a "sandwich" structure. The hollow body (1) can comprise one or several of such modules, and optionally additionally at least one separate barrier (5) or liquid-permeable element (4).

It is preferred that the barrier (5) and the optional liquid-permeable element (4) or the module comprising both are either sized in a way that thy fit exactly into the hollow body, flushing with all of the side walls of said hollow body, or that they are placed in or are connected with a holder (7) which fits exactly into the hollow body, flushing with all of the side walls of said hollow body. Any remaining gap might be filled with an adhesive or sealing material. The barrier (5) and the optional liquid-permeable element (4) can be fixed at the predetermined point by using a clamping ring or grid below the barrier (5) and/or the optional liquid-permeable element (4).

If no holder (7) is used, it is either preferred that the hollow body comprises at least one flange or support element for any of the liquid-permeable element(s) (4) or the barrier(s) (5) or both whereon the element (4) or the barrier (5) can bear, or the barrier (5) or element (4) are placed upon a support element which is transfixed inside the hollow body (1) or the barrier (5) can bear, or the barrier (5) and/or the liquid-permeable element (4) is contacted with the side walls via a suitable adhesive like e.g. a silicon adhesive, a cross-linking resin, a gum, a thermoplastic or thermosetting polymer or. The type of adhesive is not limiting the invention as long as it is not reactive with one of the ingredients added into the inventive device if used as intended. In a further embodiment the hollow body (1) is conical and the liquid-permeable element (4) and/or the barrier (5) are sized in a way that they fit only at a predetermined place inside of the hollow body (1) and are placed at this predetermined place by pressing the element (4) or the barrier (5) on said place where they are kept by tension. In any of the embodiments it might be advantageous to seal any remaining gap between the liquid-permeable element (4) and/or the barrier (5) or the holder (7) with a suitable sealing material. Suitable sealing materials are e.g. silicone polymers, thermoplastic or thermosetting polymers or resins.

Optionally the hollow body (1) can be charged additionally with (a) component(s) or material(s) which punctures cuts or ruptures the barrier material, if this obtainable effect is not already provided by e.g. the liquid-permeable element (4).

According to the desired use, e.g. the desired biomolecule isolation or purification method, the hollow body (1) further can be at least partially filled with any material which is suitably used within such an isolation or purification method. In a preferred method any chromatographic, chelating, binding, absorbing, adsorbing or filtering material is added into the hollow body, like for example Chelex resin, silicate particles or fibers, ion exchanging materials or any similar. In a particularly preferred embodiment the hollow body is at least partially filled with a chelating resin, not binding the biomolecule of interest, e.g. Chelex resin for nucleic acid isolation.

The present invention further includes a kit for collecting, storing or treating a biological sample or for isolation of a biomolecule from a biological sample, comprising a device as described above.

EXAMPLES

Example 1: Foil as Barrier Material for Lysis

Figure 3:
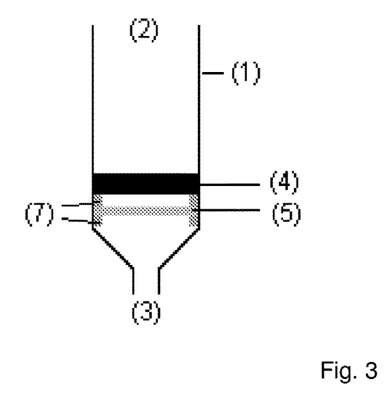
FIGS. 3, 4 and 5 show further embodiments as explained in the Examples.

In the first test very thin polyethylene foil (plastic wrap or cling film) was used as barrier (5) material in a spin column. The foil was fixed by two clamping rings as holder (7). Additionally a frit was used as liquid permeable element (4) (FIG. 3). The spin column was inserted in a collection tube. The spin column was filled with 500 µl buffer ATL (with detergent) or 500 µl buffer P1+25 mg Chelex. Afterwards the assembly was incubated at 65° C. (to reach 56° C. in the sample) for 1 h at 1000 rpm shaking. During the incubation the assembly was still sealed. After a centrifugation step of 3000×g, 1' the foil was perforated and the liquid could pass the spin column.

Example 2: Incubation with Different Lysis Buffers with the Polyethylene Foil as Barrier To show that the foil is leak-proof for lysis incubation was shown with different lysis buffers. Sample material was saliva.

Figure 4:
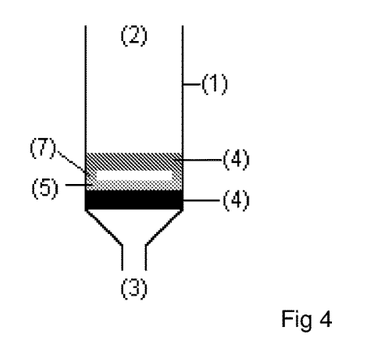

The assembly was build like in FIG. 4, there were two different frits as liquid permeable elements and a polyethylene film as barrier in the middle of the two frits. In half of the samples the assembly was fixed with two clamping rings as holder (like FIG. 5). As lysis buffers were used: ATL+20 µl ProtK, G2+20 µl ProtK, AL, MTL. The samples were incubated for 1 h at 65° C. (to reach 56° C. in the sample). The samples/barrier were closed for the whole incubation. After centrifugation at 13.000 rpm, for 1 minute the sample was in the breakthrough. In this example the device was used as pre-treatment (lysis) in front of a nucleic acid preparation with silica.

Example 3: Different Centrifugation Speeds as External Force to Make the Barrier Liquid Permeable The assembly was build like in FIG. 4 shown with two different frits. It were used 400 µl of ATL buffer. In this test different lower centrifugation speeds were used.

| No. | *g | rpm | Breakthrough of the sample | Volume of breakthrough |
|---|---|---|---|---|
| 1 + 2 | 6000 | 7516 | Yes | 400 µl |
| 3 + 4 | 5500 | 7196 | Yes | |
| 5 + 6 | 5000 | 6861 | Yes | |
| 7 + 8 | 4000 | 6137 | Yes | |
| 9 + 10 | 2000 | 4339 | Yes | 360 µl |

For lower speed it was visible, that the foil had perforations where it was pressed against the frit.

Example 4

Figure 5:
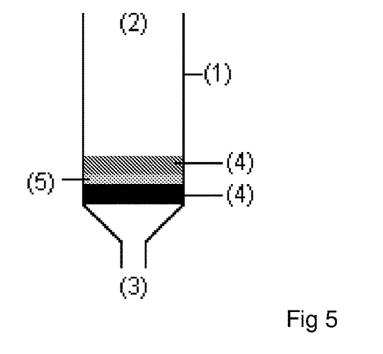

The assembly was according to FIG. 5. As samples material swabs with saliva were used and lysed in this assembly with 380 µl ATL+20 µl ProtK, over night at 60° C. and 900 rpm. The samples were still sealed after this incubation and were then centrifuged at 6000×g for 1 minute. The samples breatrough was used for a silica prep.

The yield, determined by PCR, was a little lower for the use of the device than in the standard procedure.

The invention claimed is:

1. A device, comprising (i) at least one hollow body, each hollow body having at least one open end; (ii) at least one barrier placed inside or at one end of the hollow body; (iii) at least two liquid-permeable elements inside the hollow body; and (iv) optionally at least one removable closing device to seal at least one open end;
   wherein the barrier is non-permeable for liquids and solids under ambience conditions, but becomes liquid-permeable by applying an external force to said barrier,
   the barrier is placed between the at least 2 liquid permeable elements and is in direct contact with at least one of said elements, and
   the liquid-permeable elements are selected independently from a frit, filter, fleece, and membrane, and are in contact with all of the inner side walls of the hollow body of the device and flush with said side walls.

2. The device of claim 1, wherein the external force is pressure, drag force or driving power.

3. The device of claim 1, wherein each hollow body has an inlet and an outlet; at least one barrier and at least one liquid-permeable element are placed above the outlet; and the device comprises optionally at least one collection tube to collect a mobile phase (eluate) after having passed the outlet.

4. The device of claim 1, wherein the barrier is a film, foil, coating, septum, membrane, hydrophobic sintered material, or hydrophobic fibrous material.

5. The device of claim 1, wherein the hollow body is at least partially cylindrical or conical.

6. The device of claim 5, wherein the device is a reaction tube, a reaction cup, a collection tube, a collection container, a column body, a spin column, a centrifugation tube, a microcentrifuge tubes, or a compartmented container.

7. The device of claim 6, wherein the compartmented container is a tube, cup, flask, chromatographic column, spin column, plastic syringe, multiwell plate, multiwell block, multiwell column plate, bottle, phiol, collection vessel, or centrifugation vessel.

8. The device of claim 1, wherein the barrier becomes porous by applying pressure, drag force or driving power, or has a predetermined orifice that opens or breaks by applying pressure, drag force, or driving power.

9. The device of claim 8, wherein the barrier has a predetermined orifice that breaks at a predetermined breaking point by applying pressure, drag force, or driving power.

10. The device of claim 1, wherein the device comprises, inside the hollow body and above or below of the barrier, a material or component that punctures, cuts, or ruptures the barrier when pressure, drag force or driving power is applied to the device.

11. The device according to claim 8, wherein the obtained liquid-permeability is irreversible when the external force is removed.

12. A method for preparing a device of claim 1, comprising:
   placing at least two liquid-permeable elements into a hollow body, and
   placing at least one barrier into or at the end of a hollow body,
   wherein the barrier is non-permeable for liquids and solids under ambience conditions, but becomes liquid-permeable by applying pressure, drag force, or driving power, the barrier is placed between the at least 2 liquid permeable elements and is in direct contact with at least one of said elements, and the liquid-permeable elements are selected independently from a frit, filter, fleece, and membrane.

13. A method for isolation or purification of at least one biomolecule of interest from a sample comprising at least one type of biomolecules, comprising:
   (a) placing the sample or lysate thereof inside the hollow body of a device of claim 2, wherein either the sample is a liquid sample, or the sample is contacted with any liquid before or after placing the sample inside of the hollow body, or the hollow body comprises a liquid coming in contact with the sample when said sample is placed into the device,
   (b) optionally incubating the sample inside the hollow body,
   (c) applying pressure, drag force, or driving power to the sample-comprising inner side of the device, and
   (d) collecting an eluate comprising the biomolecule of interest.

14. The method of claim 13, wherein the hollow body of the device further comprises a solid matrix and/or at least one liquid before the biological sample or lysate thereof is added.

15. The method of claim 13, wherein the hollow body has an inlet and an outlet, and wherein in step (c),
   (A) pressure is applied to the inlet of the device, pressing the biomolecule of interest to the outlet side of the device;
   (B) vacuum is applied to the outlet of the device, sucking the biomolecule of interest to the outlet side of the device;
   (C) centrifugal forces are applied to the device moving the biomolecule of interest to the outlet side of the device; or
   (D) a combination of said forces (A), (B) and/or (C) is applied to the device.

16. A kit for isolating a biomolecule from a biological sample, comprising a device of claim 2 and a material suitable for filling the hollow body of the device to isolate the biomolecule from the biological sample.

17. A method for collection, storage or treatment of a liquid-containing sample or a biomolecule-containing sample, comprising: collecting, storing, or treating a liquid-containing sample or a biomolecule-containing sample in a device of claim 1.

18. The method of claim 17, wherein the external force is pressure, drag force or driving power.

* * * * *